United States Patent
Rasmussen

[11] Patent Number: 5,823,965
[45] Date of Patent: Oct. 20, 1998

[54] DEVICE FOR REFLECTOMETRIC EXAMINATION AND MEASUREMENT OF CAVITIES

[75] Inventor: Steen Barbrand Rasmussen, Lynge, Denmark

[73] Assignee: RhinoMetrics A/S, Denmark

[21] Appl. No.: 836,457

[22] PCT Filed: Nov. 14, 1995

[86] PCT No.: PCT/DK95/00454

§ 371 Date: May 14, 1997

§ 102(e) Date: May 14, 1997

[87] PCT Pub. No.: WO96/14797

PCT Pub. Date: May 23, 1996

[30] Foreign Application Priority Data

Nov. 15, 1994 [DK] Denmark ................. 1304/94

[51] Int. Cl.[6] .................................................. A61B 8/00
[52] U.S. Cl. .......................................... 600/462; 600/529
[58] Field of Search ..................... 600/529, 532, 600/533, 452, 568, 462; 128/898, 207.14–207.15

[56] References Cited

U.S. PATENT DOCUMENTS

| | | | |
|---|---|---|---|
| 4,326,416 | 4/1982 | Fredberg | 73/597 |
| 4,561,446 | 12/1985 | Hetz | 600/452 |
| 5,152,291 | 10/1992 | Dias | 600/468 X |
| 5,190,045 | 3/1993 | Frazin | 600/468 X |
| 5,311,863 | 5/1994 | Toppses et al. | 128/207.15 |
| 5,316,002 | 5/1994 | Jackson et al. | 128/898 X |
| 5,331,967 | 7/1994 | Akerson | 600/529 |
| 5,333,614 | 8/1994 | Feiring | 600/468 X |
| 5,445,144 | 8/1995 | Wodicka et al. | 128/207.14 |
| 5,666,960 | 9/1997 | Fredberg et al. | 128/716 |

FOREIGN PATENT DOCUMENTS 95 01127  1/1995  WIPO.

*Primary Examiner*—Francis Jaworski
*Attorney, Agent, or Firm*—Ostrolenk, Faber, Gerb & Soffen, LLP

[57] ABSTRACT

An apparatus and method for reflectometric examination and measurement of human or animal cavities such as air and food passages, the device having a flexible hose which is introduced into the cavity with the distal end of the hose placed past the zone of the passage to be examined. A transducer converts an activation signal from a signal generator to an excitation signal which is sent into the interior of the hose. A response signal which depends on the local deformation of the hose in the examined zone is picked up by a transducer and subjected to analysis in relation to the excitation signal. An analysis circuit and computer give an image on screen indicating the results of the examination.

26 Claims, 3 Drawing Sheets

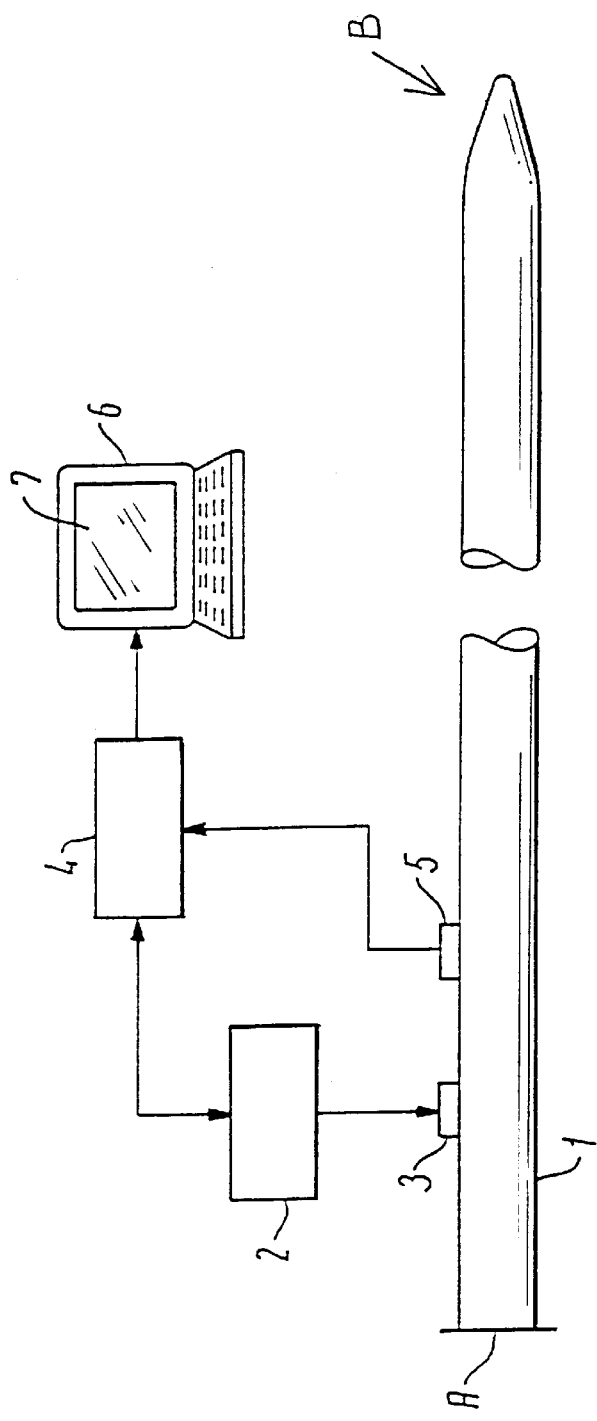
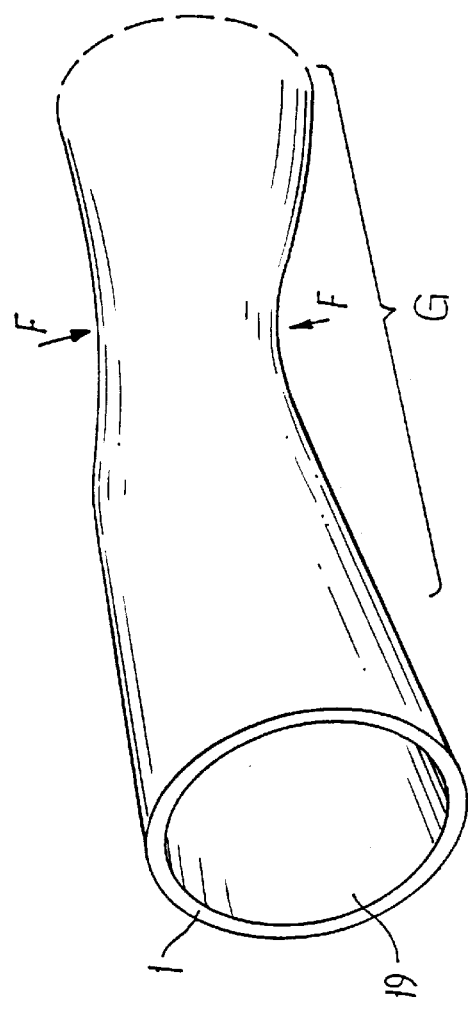
FIG.1
FIG.2

DEVICE FOR REFLECTOMETRIC EXAMINATION AND MEASUREMENT OF CAVITIES

BACKGROUND OF THE INVENTION

1. Field of the Invention

The present invention relates to a device for examination and measurement of constrictions or passages in cavities by means of acoustic reflectometry, the device comprising an electric signal source, a hose with a distal end to be introduced through an entrance to a cavity, a first transducer for transfer of an activation signal from the signal source to and through the hose, a second transducer for reception of response signals from the hose, the first and second transducers being connected with the hose close to its proximal end, and a computer adapted for analysis of the response signals in relation to the activation signal.

2. Background Art

For examination and measurement of blockings, deformations, movements etc. in various human and animal cavities, e.g. pharynx, larynx and other air and alimentary passages, arteries etc. various methods are known.

In catheter examinations, balloon-angioplasty etc. it is known to use a probe in the shape of a hose of flexible material.

Another method is based on measurement of reflection (reflectometry) using an acoustic, transient excitation signal which, through a hose and through the patient's mouth, is sent into the air passages of the patient, cf. e.g. U.S. Pat. No. 4,326,416.

Another method based on the use of a non-transient excitation signal—random or pseudorandom signal—is used in an equipment manufactured by the applicant firm, under the commercial designation SRE 2000 and SRE 2000 PC.

Especially in connection with examination of movements in the air passages and examination of stertorous respiration mainly pressure transducers, placed in or on catheters to be introduced in nose or mouth, have so far been used. This allows for measurement of pressure variations, constrictions, etc. in nose and throat.

A drawback in this technique is to be seen in that the measurement probe must include a relatively large number of closely located pressure transducers connected to a corresponding apparatus which offers the possibility, on a screen with a sufficient resolution, to determine the position of and pressure at each examined spot.

Known techniques also include endoscopy by which optical examinations are made of nose, pharynx and other internal organs. However, these examinations have a certain number of limitations, including the clarity and size of the optical image, the size of the catheter and especially the lack of catheter flexibility which makes, the catheter unsuitable for examination of, e.g., stertorous respiration.

CT and MRI scannings have been tried, but involve long periods of measurement which do not give useful measurements and no dynamic measurements at all.

By using acoustic reflectometry of the above mentioned kind, it is known that it is possible to measure across-sectional areas in the air passages as a function of the distance from the transducer used for emission of the excitation signal, cf. the above patent U.S. Pat. No. 4,326,416 or an article: "Airway geometry by analysis of acoustic pulse response measurements" by Andrew C. Jackson et al. in J. Appl. Physiology, 43(3): 525–536, 1977.

Direct measurement limits measurements of cross modes, i.e. cross resonance, and of the adjacent cavities, which, to a large extent, limits the use of such direct measurements having large differences in the cross-sectional areas as a function of the distance from the signal source.

Especially when examining stertorous respiration, the use of direct measurements is hampered by the transient or continuous sound influence, necessary for the measurements, which affects the sleep state or awakens the patient during the examination phase itself, and also causes measurement errors because of noise from the measurement microphone and a measurement error due to the very large cavity made up by the mouth and throat.

SUMMARY OF THE INVENTION

The invention aims at remedying the above mentioned disadvantages and in order to do so a device of the type mentioned in the introduction is according to the invention characterised in that the hose at least in a measuring zone is designed with a thin outer wall of a soft and/or flexible plastics or elastomeric material, and that the measuring zone is positioned at or near a distance from the distal end of the hose.

By the hose at least in a measuring zone being designed with a thin outer wall of a soft and/or flexible plastics or elastomeric material, it is attained that the position or movement of the walls of the cavity is transferred to a corresponding position or movement of the thin outer wall of the hose through abutment of the wall of the hose against the walls of the cavity.

By the measuring zone being positioned at or near a distance from the distal end of the hose, it is attained that the measuring zone may be positioned in constrictions or passages to be examined or measured by advancing the distal end of the hose through the cavity and past the constructions or passages, respectively.

The invention is based on the recognition that humans have many spots where a contracted or pathological change or obstruction in the air passages, urinary system, etc. can be difficult to determine, locate and measure with the above mentioned known technique, among other things because of the common cross resonance in the large or small surrounding cavities at the spot which is to be examined and that it is particularly suitable to use a very flexible hose, whose wall can be made to abut the side wall in question of the passage or can be deformed by some change, e.g. a constriction at the spot in question. By this, the measurement equipment can only "see," so to speak, the interior of the hose and clearly measure the least deformation in the inner cross-sectional area of the hose as a function of the distance from the spot in the hose where the excitation signal is emitted on to the spot or spots where a deformation or deformations appear and where the response signal originates.

According to a particular appropriate embodiment of the invention the device can be characterised in that the hose has a longitudinal, axially centered lumen surrounded by a ring-shaped wall, and around the ring-shaped wall a number of spaced, longitudinal canals separated from each other by means of essentially radial partitions.

By combining reflectometric measurements made inside the lumen of the hose and the peripheral canals or chambers it is possible with much greater sensitivity to determine the position or measure the areas in the hose which due to some local change or obstruction in the passage in question (air passage, urinary system etc.) are compressed, as well as the degree of compression.

Upon insertion of the hose it is possible, with or without action of positive or negative pressure in the lumen of the hose and/or the canals, by measuring the inner cross-sectional areas of the hose as a function of the distance, to determine the areas which are the most narrow or compress the hose locally.

In this way it is possible, in balloon examinations and freeing of arteries in case of arteriosclerosis, to check the distension (cross-sectional area per longitudinal distance) of the balloon at the end of a catheter concurrently with the inflation of the balloon.

The invention further provides a method for arranging a hose in a constriction or passage in a cavity, said hose being adapted for examination and measurement of such constrictions or passages by means of acoustic reflectometry, whereby an activation signal is transferred from a signal source via a first transducer to the hose and forwarded through the hose, and response signals from the hose are transferred via a transducer second to a computer adapted to analyze the response signals in relation to the activation signal, the hose over at least part of its longitudinal extension having at least one measuring zone of increased outer wall flexibility, by which method a distal end of the hose is introduced through an entrance into the cavity.

According to the invention, the hose is being placed with the measuring zone in the constrictions or passages to be examined or measured, by the distal end of the hose being advanced through the cavity and past the constrictions or passages, respectively, whereby the measuring zone is located in the constrictions or passages.

By advancing the distal end of the hose past the constriction or passage in the cavity, it is attained that the measuring zone, being placed behind the distal end of the hose, near this end or at a distance from it, will be kept straight during the introduction to the cavity. The measuring zone has a reduced ability to keep itself straight during the introduction into the cavity, due to the increased flexibility of the outer wall of the hose in this zone, and by advancing the distal end of the hose past the constriction or passage, the measuring zone is in fact "pulled" through the constriction or passage by a pull from the distal end of the hose.

This pull may, e.g., be exerted on the measuring zone by inserting a springy steel wire into the hose during its introduction into the cavity. The distal end of the hose is closed, so the wire will be able to push the distal end forward trough the cavity.

In preferred embodiments of the method, the cavity is an organic cavity, e.g. the respiratory passages, the blood or lymph tracts, the alimentary canal, or the urinary system or sections thereof of an animal or a human body.

Other features and advantages of the present invention will become apparent from the following description of embodiments of the invention which refers to the accompanying drawings.

BRIEF DESCRIPTION OF THE DRAWINGS

FIG. 1 shows a block diagram of the basic lay-out of the device according to the an embodiment of invention;

FIG. 2 is a perspective drawing of part of the hose, at the spot where the measurement is made;

DETAILED DESCRIPTION OF EMBODIMENTS OF THE INVENTION

Figure 4:
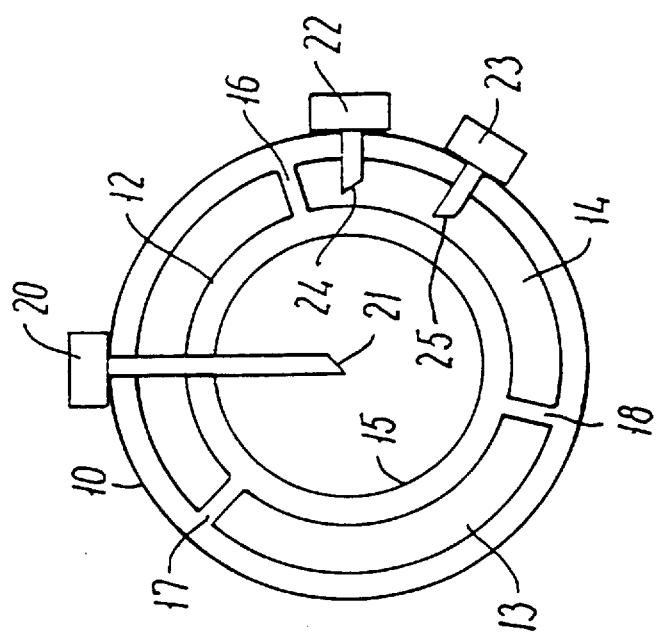
FIG. 4 is a sectional view of the hose according to FIG. 3 in a sectional plane at right angles to the axis of the hose.

FIG. 1 shows the basic lay-out of the device according to the invention.

As seen in FIG. 1, there is shown a hose 1, the design of which will be explained below. At its proximal end A, the hose 1 of a manner known per se, not illustrated, is connected to auxiliary equipment used for inserting the hose in, e.g., the air passages of a patient, through the mouth or the nostrils, or in the urinary system or an artery. The distal end of the hose B, which after insertion, will be present in the cavity of the patient who undergoes an examination.

An electronic signal generator 2 is adapted to give an activation signal to a transducer 3 connected to the hose 1. The signal generator 2 delivers the same signal to a signal analysis processor 4. A transducer 5 is connected to the hose 1. When an excitation signal is transferred from the signal generator 2, via the transducer 3, to the interior of the hose 1, this signal will propagate in the hose, on to the distal end of the hose, from where a response signal is sent back and received by the transducer 5 and from there led to the signal analysis processor 4.

The signal analysis processor 4 is connected to a computer 6 by means of which it is possible on a screen 7 to present an image which illustrates the results of the examination and measurements made.

The transducer 3 can be an arbitrary type known per se, e.g. an electromagnetic transducer, an electrostatic transducer, a piezo-electric transducer, etc. Its task is to transform the electronic signal from the signal generator 2 into an excitation signal in the interior of the hose 1.

The transducer 5 can also be of the above mentioned arbitrary type, e.g. a microphone, the purpose of which is to receive an acoustic response signal from the distal end of the hose and to transform this response signal into an electric signal which is led to the signal analysis processor 4.

The excitation signal can be a transient signal in the low frequency band, as known from, e.g., the above U.S. Pat. No. 4,326,416 or from the Jackson article. It can also be a non-transient excitation signal—a random or pseudo-random signal, as used in the above mentioned equipment SRE 2000 and SRE 2000 PC.

The invention is a very important contribution to determination of the exact position of the obstruction and to measure when and for how long the obstruction will last. It is thus possible to connect an alarm system to the measuring equipment which gives an alarm when the probe has been compressed for a certain fixed period of time.

The analysis itself of the response signal in relation to the excitation signal belongs to a technique known per se.

FIG. 2 shows part of the hose 1 in the zone G of the hose. The characteristic of the hose according to the invention is that, at least in its zone G at the distal end it is thin-walled. The hose according to FIG. 2 is a simple hose, e.g. a hose with only one lumen 19.

If the hose 1, as will be explained later, locally, e.g. in the mentioned zone G, is exposed to an external mechanical influence (as indicated at the arrow F), due to a constriction in the air passage, the oesophagus or an artery of the patient, the reduction of the cross-section of the hose in said zone G will consequently bring about a modification of the response signal, a modification which can be seen in the picture analysis and on the screen. This modification expresses the change that might be present in the patient, e.g. a constriction.

Figure 3:
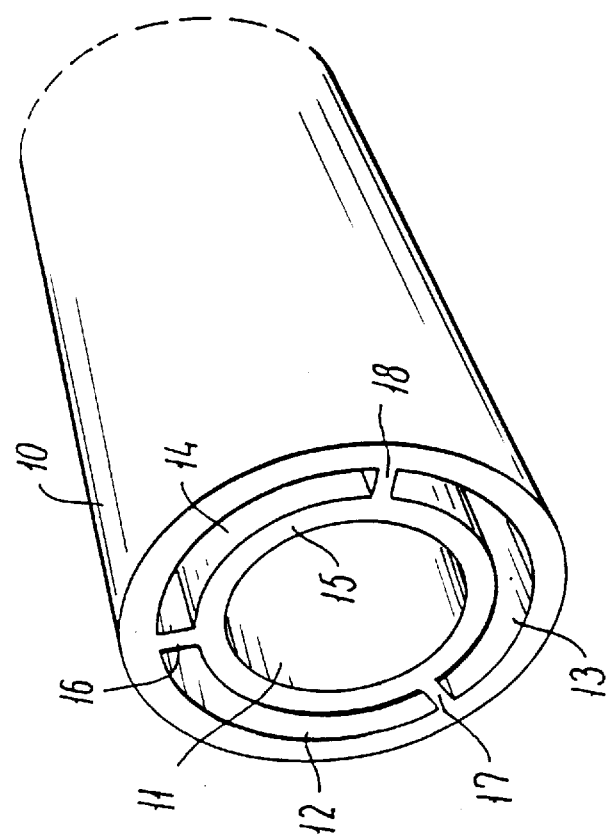
FIG. 3 is a perspective drawing of part of the hose in another embodiment of the invention.

FIG. 3 shows a further embodiment of a hose according to the invention. The hose 10 has a central lumen 11 and three peripheral annular canals or chambers 12, 13, and 14. Such a hose can be made by extrusion of a soft plastics material or elastomer. The outer diameter of the hose can vary from, e.g., 1 mm to 3–4 mm, according to the intended use. The wall 15 around the central lumen 11 is continuous in the longitudinal direction of the hose and it separates the lumen 11 from the three peripheral chambers 12, 13, 14. The chambers themselves which are also continuous in the longitudinal direction of the hose are separated from each other by means of radial partitions 16, 17, and 18.

FIG. 4 shows a cross-sectional view of the hose in a plane at right angles to the axis of the hose.

A transducer 20 has been introduced from the outside through the outer chamber 12 and through the wall 15 so that the response signal receiving end 21 of the transducer 20 is located in the lumen 11.

FIG. 4 also shows two transducers 22 and 23, which are introduced from the outside into the outer wall of the hose 15 and whose response signal receiving ends 24 and 25 respectively are located in a peripheral chamber, e.g. chamber 14.

While the sectional view in FIG. 4 shows the two transducers 22 and 23 placed in the sectional plane (the plane of the diagram) it should be understood that they do not need be it and that, e.g., transducers 23 can be placed axially displaced from the transducer 22.

Figure 5:
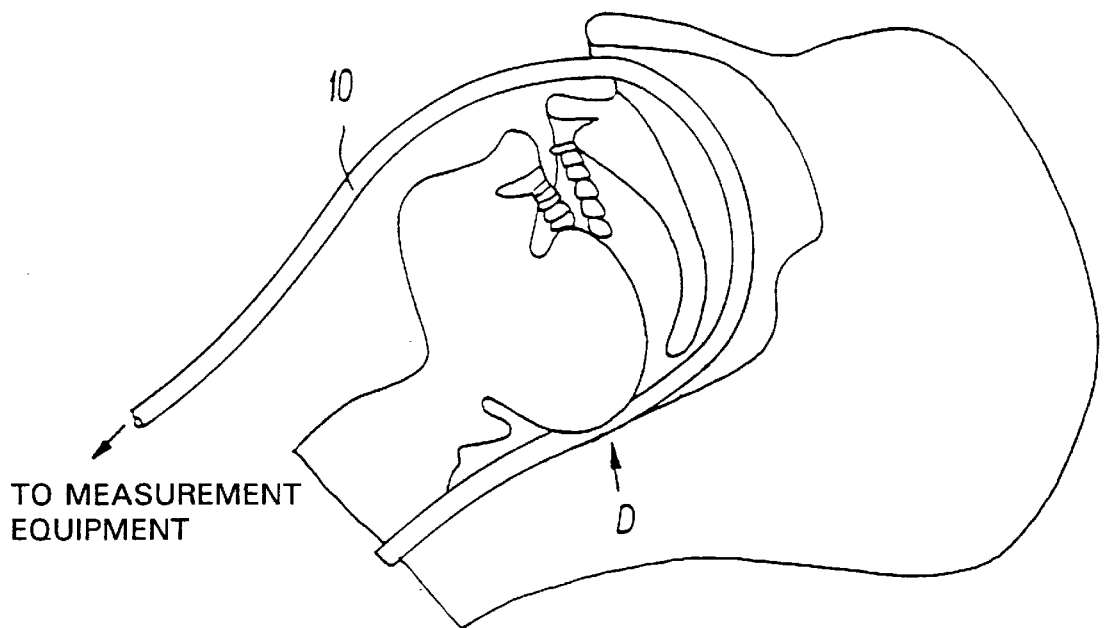
FIG. 5 illustrates the placing of a hose in the upper air passages with a patient being examined for tongue-fallback.

FIG. 5 illustrates the use of the hose in order to determine the position of and measure the so-called tongue fallback with a patient, e.g. the situation where the patient's tongue narrows the upper air passages.

Here the hose has been introduced through the nostrils and into the air passage. Part of the hose is compressed by the rear end of the tongue in the zone D.

Figure 6:
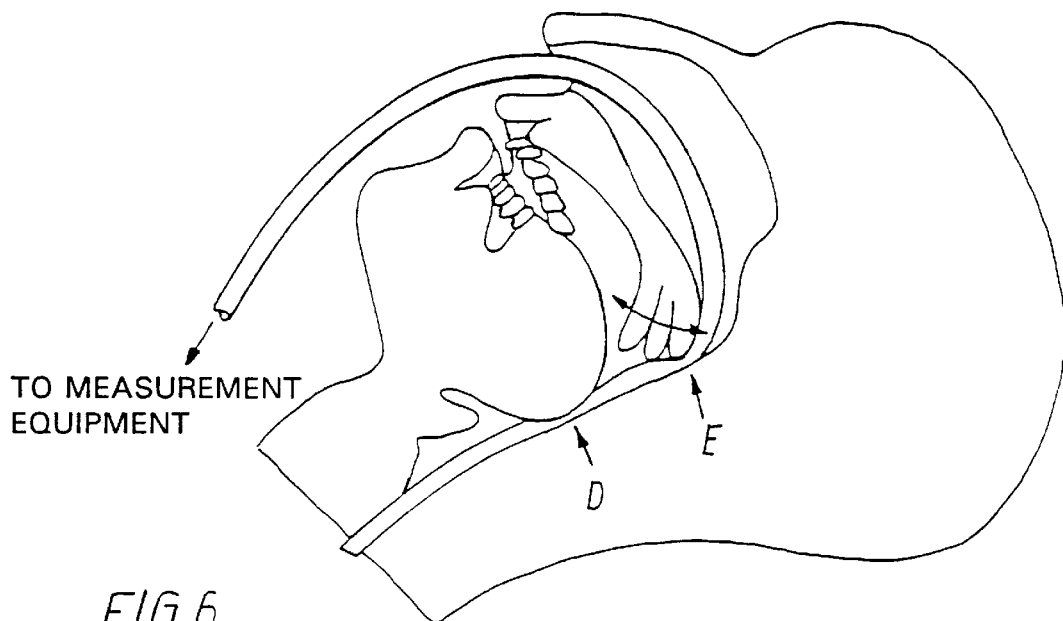
FIG. 6 illustrates the placing of a hose in the upper air passages with a patient being examined for stertorous respiration.

FIG. 6 illustrates the use of the hose in order to determine the position of and measure the outbreak of vibrations in the soft palate (velum palatum).

FIG. 6 shows the situation illustrated in FIG. 5 as well as the situation where said soft parts of the palate compress the hose in the zone E.

The mode of operation of the device according to the invention will be explained below.

It should be recalled, as mentioned in the preamble of the specification, that it is possible with the measurement technique known from U.S. Pat. No. 4,326,416 and from the Jackson article and the one used in the known measurement equipment of the applicant firm, to determine the cross-sectional area of a cavity as a function of the distance from the excitation signal giving transducer to the measurement spot.

While the known technique has the disadvantage that the measurements can be disturbed by crossmodes (e.g. cross resonances) which, e.g., is the case in examinations of the air passages and the lungs with a patient, the technique according to the invention has the essential advantage that it is the inner cavity of the hose which constitutes the measurement cavity proper, which on occasion will be modified by, e.g., a constriction in the passage in which the hose has been introduced. The construction of the hose excludes the outbreak of cross resonances as in the known technique. If the hose, which as mentioned has thin, flexible walls, is affected locally by a constriction, one or more of the outer chambers 12, 13, 14 and/or the central canal (lumen 19, FIG. 2, or lumen 11, FIG. 3) is affected mechanically by this constriction, this situation being measured immediately by the measurement equipment.

Supposing that the hose has the form shown in FIG. 3 and 4 and that it has been introduced in the patient's air passage as shown in FIG. 5. The mechanical compression force from, e.g., the rear end of the tongue on the hose can, e.g., influence one of the outer chambers, the outer chamber 14, which can be ascertained electronically in the measurement equipment, or perhaps also the second and third outer chamber.

The invention therefore offers the possibility to get a "differentiated" determination of position, and measurement of the cross sectional area in the zone in question as a function of the distance from the excitation signal sending transducer in question to the zone in question.

If it is only the outer chamber 14, as mentioned in the previous paragraph, which in a patient's air passage is influenced by, e.g., the rear end of the tongue, only the transducer(s) belonging to the chamber 14 will react.

FIG. 6 illustrates as already mentioned the situation where a patient is to be examined for vibrations in the soft parts of the palate, e.g. typically stertorous respiration. The vibrations in the zone E will influence at least one of the outer chambers of the hose and the measurement equipment can carry out the positioning and measurement.

Another field of particular medical or surgical interest for the invention is examinations of constrictions, e.g. calcification or other pathologic disorders in the arteries, e.g., at the heart.

Figure 7:
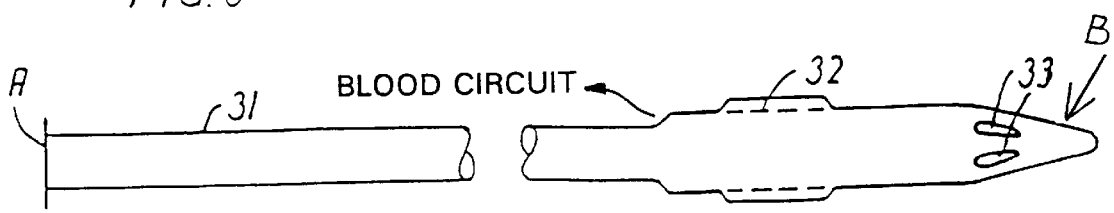
FIG. 7 shows a diagram of a hose with a balloon for a catheter examination in an artery.

FIG. 7 shows another embodiment of the hose according to the invention, made for this kind of examination.

The distal end of the hose 31 is in a manner known per se (normal catheter technique for widening blood vessels) formed as an inflatable balloon 32. It can be inflated by pressure feed through longitudinal canals (not shown) in the outer wall of the hose. Between the balloon 32 and the distal end B of the hose there is, in a manner known per se, a number of openings 33 which are to ensure blood passage and at some distance away from the balloon 32 in the direction towards the proximal end A of the hose there are outlets (not shown) for the circulating blood.

In the case where it is medically or surgically advisable temporarily to disconnect the blood circulation through the hose in order to measure and/or widen, it is possible to use a hose which does not have a canal for circulating blood, e.g. having neither openings 33 nor matching outlets.

Upon introduction of the hose it is possible, in the above mentioned way, to position and measure the constriction or the calcification and the widening, if any.

Within the scope of the invention it is possible to make a hose without the above mentioned balloon 32 and manufacture the hose so that it has, at its distal end B, e.g. where the balloon otherwise would be placed, a considerably thinner and/or considerably more flexible outer wall. Within the scope of the invention, the hose can be formed near its proximal end A with means (not shown) so as to establish a negative or positive pressure, e.g. of fluid in the lumen and/or in each chamber. Such a positive pressure will bring about a dilation of said thinner and/or more flexible part of the hose at the distal end. Whether the hose has a balloon 32 or not, whether it is inflated or not and whether one or more chambers are compressed by the constriction in the vein, the measurement equipment will give a picture of the situation in the area in question.

A description of a hose has been given above with one single lumen or with one central lumen and peripheral chambers, but it is within the scope of the invention to allow for a hose with two axial canals or a central lumen and, e.g., two, four or five peripheral chambers.

Obviously medical or surgical considerations decide the choice of the inner and outer dimensions of the hose which is the reason why the hose is manufactured in different sizes (and lengths too), while the measurement equipment decides the upper frequency limit, if a transient signal is used, as well as the other physical parameters.

If the hose according to the invention is to be used for examination of the breathing organs, the needed supply of air or gas to the patient can take place through the inlet of the hose (A in FIG. 1) and through a canal to the openings 33 (FIG. 7) at the distal end of the hose. In that case the response signal which comes from, e.g. one or several of the peripheral chambers, can be separated electronically in the measuring equipment from the response signal coming from the lungs, due to the difference in the signal transit time.

A particular example of the use of the invention has already been mentioned.

Exact examinations of persons, whose air passages are blocked during their sleep and who can be described as having stertorous respiration, are naturally very difficult and through the ages many failed corrective operations have been made on these patients.

The invention is a very important contribution to determine the exact position of the blocking and to measure when and for how long the blocking will last. It will therefore be possible to connect an alarm system to the measuring equipment which gives an alarm when the probe has been compressed for a certain fixed period of time.

Today a pulsoxymeter (instrument measuring the concentration of oxygen in blood) is connected during these examinations. An alarm is therefore activated when the concentration reaches certain predetermined limits.

It is not the stertorous respiration itself which is a risk, but the period during which the patient does not breathe because of a blocking.

This is the reason why equipment which acoustically registers the stertorous respiration does not activate an alarm with sufficient security, as the non-occurrence of a "snoring sound" is either due to a quiet, steady respiration with a low regular flow, which is all right, or the air passages being blocked for a long time. This is where the risk lies.

In order to stress the importance of the invention it should be mentioned that the under-supply of oxygen to the lungs for such a long time considerably increases the risk of brain damages and thrombosis, especially for older overweight persons.

An internal measurement has the advantage that the patient is not awakened during the measurements by the excitation signal and at the same time the measurements are not influenced to a large extent by the high tone sound spectrum of the snoring sounds.

The measurement probe itself is very easy to introduce ambulatory into the patient's nose before the night, in cooperation with a doctor or a nurse.

A correct "tightening" through the nose happens automatically due to the reflectory swallowing, and a connection (transducer/microphone part) at the end which projects out of the nose can be made without problems.

A synchronization of the area measurements with the snoring sound is easy to make either by means of an external microphone, e.g. one of the transducers 22 and 23, (FIG. 4) or by using the low frequency signal received through the measurement microphone.

It should also be noted that the measurement equipment (hardware/software) which adequately makes the measurements in each chamber and during the measurements changes the static pressure in each chamber can also concurrently give information about the elasticity of the tissue giving counter-pressure to the surface of the chambers.

By establishing a pressure in the hose and a concurrent supply of acoustic energy in the infrasound band up to 200 Hz in the lumen and the chambers and a synchronization of this infrasound signal with the acoustic rhinometry (reflectometric) measurements, it is possible to obtain valuable information about the elasticity in the walls to which the hosewall establishes a contact during the various pressure conditions.

Considering that these kinds of transducers, e.g. a piezoelectric transducer function in both directions, e.g. being applied an electric voltage in order to give a pressure signal, or receiving a pressure signal and give an electric signal, it is obvious that instead of two transducers 3 and 5 in FIG. 1 it is in principle possible to use one single transducer, in which case the signal generator 2 should be electronically designed in such a way that, when operated from the analysis unit 4 and the computer 6, it firstly gives a transient signal and then transfers the response signal to the analysis unit. If a random or a pseudo-random signal is used as excitation signal, emitted continuously in the measurement period, two separate transducers will be used, as shown in FIG. 1.

It should also be added that the invention also offers the possibility of making prostate or uterus examinations etc.

Finally, it should be mentioned that the invention also offers a possibility to make reflectometric examinations of other cavities, e.g. current control of the cavity in an item manufactured by extrusion, as the technique according to the invention makes it possible to closely monitor the extrusion parameters in order, e.g., to obtain a constant thickness of walls in the item, which could, e.g., be a hose.

I claim:

1. A device for examination and measurement of constrictions or passages in a cavity by means of acoustic reflectometry, comprising:
    (a) an electric signal source;
    (b) a hose having a closed distal end to be introduced through an entrance to the cavity, and a proximal end;
    (c) a first transducer for converting an activation signal from said electric signal source into an acoustic excitation signal and supplying said excitation signal to and through said hose;
    (d) a second transducer for reception of acoustic response signals generated in response to said excitation signal and propagated through said hose, said first and second transducers being connected with said hose close to said proximal end; and
    (e) a signal analysis processor being connected with said first and second transducer for analysis of said response signals in relation to said excitation signal so as to determine the internal cross-sectional shape of said hose;
said hose having an outer wall of a soft or elastomeric material, at least in a measuring zone of said hose, and said measuring zone being movable so as to change its cross-sectional shape in response to said constrictions or passages of said cavity to be examined and measured.

2. A device according to claim 1, wherein said hose has one longitudinal canal.

3. A device according to claim 1, wherein said hose has two longitudinal canals separated from each other by a substantially diametrical partition.

4. A device according to claim 1, wherein said hose has a longitudinal, axially centered canal surrounded by a substantially cylindrical wall, and said hose further comprises a plurality of longitudinal chambers, spaced around said cylindrical wall and separated from each other.

5. A device according to claim 4, wherein said plurality of longitudinal chambers comprise three chambers, each substantially having a cross-sectional shape which is a section of an annular ring, wherein said three chambers cover substantially equal angular ranges of said annular ring.

6. A device according to claim 4, wherein said hose has means at its proximal end for establishing a negative or positive pressure relative to surrounding pressure, in one or more of said canals.

7. A device according to claim 4, wherein said hose has a longitudinal shunt canal extending through the length of said measuring zone for circulation past said measuring zone of fluid flowing in said cavity, said longitudinal shunt canal at least over a part of its extension being constituted by said longitudinal, axially centered canal.

8. A device according to claim 1, wherein said hose at least in said measuring zone has an increased flexibility of said outer wall relative to said outer wall in other parts of said hose.

9. A device according to claim 8, wherein said outer wall in said measuring zone has a locally reduced wall thickness relative to said outer wall in other parts of said hose.

10. A device according to claim 8, wherein said outer wall in said measuring zone comprises a wall material different from said wall material in other parts of said hose.

11. A device according to claim 1, wherein said hose has means at its proximal end for connecting said hose to auxiliary equipment to introduce said hose into said cavity.

12. A device according to claim 11, wherein said auxiliary equipment is a springy wire.

13. A device according to claim 1, wherein said first and second transducers comprise a common electro-acoustic transducer.

14. A device according to claim 13, wherein said proximal end of said hose is adapted for attachment of said common electro-acoustic transducer for supply of said excitation signal from said signal source to one or more of said canals, and for transfer of said response signals from one or more of said canals to said signal analysis processor.

15. A device according to claim 1, wherein said first and second transducers each comprise a separate electro-acoustic transducer.

16. A device according to claim 15, wherein said proximal end of said hose is adapted for attachment of said separate electro-acoustic transducers for supply of said excitation signal from said signal source to one or more of said canals, and for transfer of response signals from one or more of said canals to the signal analysis processor, respectively.

17. A device according to claim 1, wherein said hose has a longitudinal shunt canal extending through the length of said measuring zone for circulation past said measuring zone of a fluid flowing through said cavity.

18. In combination with an organism having a cavity, the device according to claim 1, wherein said hose is disposed within said cavity.

19. A combination according to claim 18, wherein said cavity is a respiratory passage of an animal or a human being.

20. A combination according to claim 18, wherein said cavity is a blood or lymph tract of an animal or human being.

21. A combination according to claim 18, wherein said cavity is an alimentary canal or a urinary system of an animal or human being.

22. A method for examination and measurement of constrictions or passages in a cavity by means of acoustic reflectometry, comprising the steps of:

(a) arranging a hose in said cavity, by introducing a closed distal end of said hose through an entrance into said cavity, said hose over at least part of its longitudinal extension having at least one measuring zone which is movable so as to change its cross-sectional shape in response to said constrictions or passages of said cavity to be examined and measured;

(b) placing said hose with said measuring zone in said constriction or passage to be examined and measured, by advancing said distal end of said hose through said cavity and past said constriction or passage, respectively, whereby said measuring zone is located in said constriction or passage;

(c) transferring an activation signal from an electrical signal source via a first transducer to said hose and further on through said hose; and (d) transferring response signals from said hose via a second transducer to a signal analysis processor which is adapted to analyze said response signals in relation to said excitation signal so as to determine the internal cross-sectional shape of said hose.

23. A method according to claim 22, wherein said cavity is a cavity in an organism.

24. A method according to claim 23, wherein said cavity is a respiratory passage of an animal or a human being.

25. A method according to claim 23, wherein said cavity is a blood or lymph tract of an animal or human being.

26. A method according to claim 23, wherein said cavity is an alimentary canal or a urinary system of an animal or human being.

* * * * *